United States Patent
Togashi et al.

(10) Patent No.: US 10,258,545 B2
(45) Date of Patent: Apr. 16, 2019

(54) OILY COSMETICS

(71) Applicant: TOKIWA CORPORATION, Nakatsugawa-shi, Gifu (JP)

(72) Inventors: Shunsuke Togashi, Kawaguchi (JP); Kazunori Ogino, Kawaguchi (JP)

(73) Assignee: TOKIWA CORPORATION, Nakatsugawa-shi, Gifu (JP)

( * ) Notice: Subject to any disclaimer, the term of this patent is extended or adjusted under 35 U.S.C. 154(b) by 0 days.

(21) Appl. No.: 15/818,749

(22) Filed: Nov. 21, 2017

(65) Prior Publication Data

US 2018/0140512 A1     May 24, 2018

(30) Foreign Application Priority Data

Nov. 22, 2016   (JP) ................ 2016-226680

(51) Int. Cl.
| | |
|---|---|
| A61K 8/31 | (2006.01) |
| A61K 8/02 | (2006.01) |
| A61K 8/37 | (2006.01) |
| A61K 8/49 | (2006.01) |
| A61K 8/891 | (2006.01) |
| A61K 8/92 | (2006.01) |
| A61Q 1/06 | (2006.01) |
| A61Q 1/08 | (2006.01) |
| A61Q 1/10 | (2006.01) |
| A61K 8/55 | (2006.01) |
| A61K 8/58 | (2006.01) |
| A61Q 1/04 | (2006.01) |

(52) U.S. Cl.
CPC ............ *A61K 8/022* (2013.01); *A61K 8/31* (2013.01); *A61K 8/37* (2013.01); *A61K 8/498* (2013.01); *A61K 8/553* (2013.01); *A61K 8/585* (2013.01); *A61K 8/891* (2013.01); *A61K 8/922* (2013.01); *A61Q 1/06* (2013.01); *A61Q 1/08* (2013.01); *A61Q 1/10* (2013.01); *A61K 2800/31* (2013.01); *A61K 2800/622* (2013.01); *A61Q 1/04* (2013.01)

(58) Field of Classification Search
CPC .... A61K 2800/622; A61K 8/022; A61K 8/31; A61K 8/37; A61K 8/498; A61K 8/891; A61K 8/922; A61Q 1/04; A61Q 1/06; A61Q 1/08; A61Q 1/10
See application file for complete search history.

(56) References Cited

U.S. PATENT DOCUMENTS 5,266,321 A * 11/1993 Shukuzaki ............. A61K 8/375
                                                                   424/401
6,482,441 B1* 11/2002 Hasegawa ................ A61K 8/11
                                                                   424/490

FOREIGN PATENT DOCUMENTS

| JP | 2002-322015 | 11/2002 |
|---|---|---|
| JP | 2010-077111 | 4/2010 |
| JP | 2013-079264 | 5/2013 |
| JP | 2014-189497 | 10/2014 |

* cited by examiner

*Primary Examiner* — Ernst V Arnold
(74) *Attorney, Agent, or Firm* — Soei Patent & Law Firm

(57) ABSTRACT

Oily cosmetics which exhibit sufficient filling properties of viscosity and fluidity during the heating and melting steps of manufacture, significantly ameliorate the problems associated with the aggregation of powder, and have excellent usability characteristics, contain coated powder obtained by subjecting base material powder to composite treatment using at least alkylsilane and phospholipid through a wet method. The oily cosmetics contain 5 to 65 mass % of powder component, 0 to 40 mass % of solid oil, and 25 to 95 mass % of liquid oil, in which the content of the coated powder in the powder component is 0.1 to 65 mass % based on the total amount of the oily cosmetics.

18 Claims, No Drawings

OILY COSMETICS

CROSS-REFERENCE TO RELATED APPLICATIONS

This application claims the benefit of priority from Japanese Patent Application No. 2016-226680, filed Nov. 22, 2016, the entire contents of which are incorporated herein by reference.

FIELD

This application generally relates to oily cosmetics.

BACKGROUND

Oily cosmetics are used for the purpose of softening or protecting the skin, hair, or the like. Particularly, solid type oily cosmetics are easily applied and are conveniently carried. Therefore, the solid type oily cosmetics are applied to cosmetics for various applications including makeup cosmetics such as lipstick, foundation, and blush, skin care cosmetics such as eye cream, antiperspirant, and solid perfume, and hair cosmetics such as hair dressing agents.

Oily cosmetics which are formed in a stick shape and are stored in an extension type container are used in an eyebrow pencil, eyeliner, eye shadow and the like. Oily cosmetics which are melted, filled in an inner tray of a compact, cooled, and solidified are used as foundation and the like. In some cases, pigment powder is blended with these oily cosmetics as a coloring agent. However, when the oily cosmetics are heated and dissolved so as to be in a liquid phase in the process of filling a stick type container or an inner tray container with the oily cosmetics, in some cases, the pigment powder aggregates to form a striped pattern or the like, thereby impairing the appearance. Particularly, pigment powder is blended in a high concentration in order to increase coloring power in an eyebrow pencil, eyeliner, and the like, and therefore, it is difficult to obtain fluidity of the oily cosmetics during heating and dissolving. Thus, in some cases, it is difficult to fill a container with the oily cosmetics. In addition, the oily cosmetics with which the powder is highly concentrated tend to be hard to use.

A method for adjusting oily components (for example, following Japanese Unexamined Patent Publication No. 2014-189497) or a method for modifying a lipophilic treatment agent on the surface of powder is known as a method for improving dispersibility of powder in oily cosmetics. It is also known that the properties of the treatment agent regarding the coated powder are expressed while using the cosmetics (for example, Japanese Unexamined Patent Publication No. 2002-322015 and Japanese Unexamined Patent Publication No. 2010-77111). In addition, a method for making powder highly functional by coating the powder with a combination of a plurality of surface treatment agents has also been proposed (for example, Japanese Unexamined Patent Publication No. 2013-79264).

However, the oily cosmetics in the related art fail to achieve all of the desired characteristics of fluidity, color uniformity, and usability at a high level in the same cosmetic product. For example, some prior art oily cosmetics do not have sufficient viscosity or fluidity during the heating and melting steps of manufacturing, while other prior art oily cosmetics fail to adequately suppress color floating problems due to the aggregation of powder. Still other prior art oily cosmetics exhibit usability problems such as greasy feeling and insufficient coverage due to clumping. Therefore, further improvement is required.

The present invention has been made in consideration of the above-described circumstances, and an object of the present invention is to provide oily cosmetics which exhibit sufficient filling properties of viscosity and fluidity during heating and melting, such as when preparing the oily cosmetics to be filled into a mold or container. Additionally an object of the invention is to significantly ameliorate the problems associated with the aggregation of powder, and to provide oily cosmetics with excellent usability characteristics.

SUMMARY

The present inventors have conducted extensive studies in order to solve the above-described problems. As a result, they have found that coated powder obtained by subjecting powder to composite treatment through a specific method using two types of specific surface treatment agents exhibits sufficient dispersibility even in a case of being blended in a high concentration with oily cosmetics, and improves the filling properties such as viscosity, and also the usability of the oily cosmetics, and have completed the present invention based on these findings.

Disclosed herein is an example oily cosmetic. The oily cosmetic may comprise an oily component and a powder component comprising coated powder obtained by subjecting base material powder to a composite treatment using at least alkylsilane and phospholipid through a wet method.

The oily cosmetics of the present invention exhibit sufficient filling properties such as viscosity and fluidity during heating and melting, significantly ameliorate the problems associated with the aggregation of powder, and have excellent usability characteristics, by containing the above-described coated powder. In a case where the base material powder in the coated powder is a coloring pigment, it is possible to suppress the coloring pigment from being aggregated during heating and melting and forming a striped pattern or the like. In addition, the oily cosmetics of the present invention exhibit sufficient filling properties during heating and melting even in a case where the above-described coated powder is blended in a high concentration with the oily cosmetics, and therefore, rarely become stiff to use. Furthermore, it is also possible to make the above-described coated powder have excellent adhesiveness when applied to the skin. And the above-described coated powder makes the oily cosmetics of the present invention have excellent makeup durability such as long-wearing and sufficient adhesive.

Additionally, an example oily cosmetic may comprise 5 to 65 mass % of powder, 0 to 40 mass % of solid oil, and 25 to 95 mass % of liquid oil, in which the content of the coated powder in the powder is 0.1 to 65 mass % based on the total amount of the oily cosmetics.

The oily cosmetics of the present invention may be solid. That is, the oily cosmetics of the present invention can be regarded as solid cosmetics.

According to the present invention, it is possible to provide oily cosmetics which exhibit sufficient filling properties such as viscosity and fluidity during the heating and melting steps of manufacture, such as when preparing the oily cosmetics to be filled into a mold or container, significantly ameliorate the problems associated with the aggregation of powder, and have excellent usability characteristics.

DESCRIPTION OF THE PREFERRED EMBODIMENTS

[Oily Cosmetics]

Oily cosmetics of the present embodiment comprise powder components and oily components. An example oily cosmetic may comprise a coated powder comprising a base material powder incorporated with at least alkylsilane and phospholipid.

(Powder Components)

The oily cosmetics of the present embodiment comprise coated powder obtained by subjecting base material powder to composite treatment using at least alkylsilane and phospholipid through a wet method, as powder components.

The composite treatment performed through the above-described wet method means that at least alkylsilane and phospholipid are incorporated with the base material powder in the continuous presence of a liquid solvent. This treatment is distinguished from a dry method in that there is no step of drying a solvent between the addition of alkylsilane and the addition of phospholipid. In addition, the incorporation of alkylsilane and phospholipid with the base material powder may be performed in the order of alkylsilane and phospholipid or in a reversed order of phospholipid and alkylsilane, or both alkylsilane and phospholipid may be incorporated into the base material powder at the same time in the continuous presence of the liquid solvent.

Any base material powder can be used without particular restriction as long as it is used in usual cosmetic products. Examples of the base material powder include extender powder and a coloring pigment.

Examples of the extender powder include inorganic powder, synthetic inorganic powder, organic powder, metal soap, and synthetic polymer powder. More specific examples thereof include mica, kaolin, sericite, talc, phlogopite, synthetic mica, silica, calcium carbonate, magnesium carbonate, aluminum oxide, boron nitride, zinc stearate, aluminum stearate, zinc myristate, polyethylene powder, urethane beads, poly(methyl methacrylate), and organopolysiloxane elastomers.

Examples of the coloring pigment include red iron oxide, yellow iron oxide, black iron oxide, cobalt oxide, ultramarine blue, iron blue, titanium oxide, zinc oxide, pearl pigments (titanium mica, fish scale foil, bismuth oxychloride, and the like), organic pigments (Red No. 228, Red No. 226, Blue No. 404, Red No. 202, Yellow No. 4 Aluminum Lake, and the like), and natural pigments (carmine, safflower, and the like).

Base material powder combining two or more kinds of powder may be used.

The average particle diameter of the base material powder can be set to be 0.01 to 200 μm and 0.01 to 150 μm.

It is possible to use triethoxyalkylsilane such as triethoxycaprylylsilane and triethoxydecylsilane, and trimethoxyalkylsilane such as trimethoxycaprylylsilane and trimethoxydecylsilane as alkylsilane. Among them, triethoxycaprylylsilane and trimethoxycaprylylsilane are preferable from the viewpoints of hydrophobicity, dispersibility, and the like.

It is possible to use hydrogenated lecithin, non-hydrogenated lecithin, and the like as phospholipid. Phospholipid may be in a form of a salt such as a metal salt. Among them, hydrogenated lecithin is preferable from the viewpoints of hydrophobicity, dispersibility, and the like.

The amount of alkylsilane added is, with respect to 100 parts by mass of base material powder, preferably 0.1 to 10 parts by mass and more preferably 1 to 5 parts by mass from the viewpoints of hydrophobicity, dispersibility, and usability.

The amount of phospholipid added is, with respect to 100 parts by mass of base material powder, preferably 0.1 to 10 parts by mass and more preferably 1 to 5 parts by mass from the viewpoints of hydrophobicity, dispersibility, and usability.

The mass ratio (A/B) of the addition amount A of alkylsilane to the addition amount B of phospholipid is preferably 0.01 to 100 and more preferably 0.2 to 5 from the viewpoints of hydrophobicity and dispersibility.

The base material powder can be further treated with a surface treatment agent other than alkylsilane and phospholipid. It is possible to use a silicone type treatment agent, a fluorine type treatment agent, an amino acid type treatment agent, and the like as such a surface treatment agent.

Examples of the solvent used for the wet method include water, isopropyl alcohol, methyl alcohol, ethyl alcohol, 1-propanol, acetone, and 1-butanol.

Examples of the method for producing coated powder include the following method. A solution obtained by mixing alkylsilane, aluminum chloride, and a solvent described above with each other is added dropwise into a mixer in which a base material powder is placed, and the base material powder and the solution are sufficiently mixed with each other. Thereafter, an alkaline aqueous solution such as ammonia water is added thereto, and the mixture is further mixed together. Subsequently, phospholipid is added to the mixer and the mixture is stirred. Then, the interior of the mixer is heated and depressurized, and the solvent or the like is removed to obtain coated powder.

The order of addition of alkylsilane and phospholipid may be changed. For example, the following method is used. Phospholipid is added to a mixer in which a base material powder is placed, and the mixture is stirred. Thereafter, a solution obtained by mixing alkylsilane, aluminum chloride, and a solvent described above with each other is added dropwise into the mixer, and the base material powder and the solution are sufficiently mixed with each other. Thereafter, an alkaline aqueous solution such as ammonia water is added thereto, and the mixture is further mixed together. Then, the interior of the mixer is heated and depressurized, and the solvent or the like is removed to obtain coated powder.

By performing a composite treatment on the base material powder using alkylsilane and phospholipid through a wet method as described above, the surface of the base material powder is uniformly covered with these treatment agents, and therefore, it is possible to obtain temporal stability. In such coated powder, it is possible to obtain oil dispersibility and usability in a high level when the coated powder is blended with oily cosmetics. In addition, the coated powder also has excellent adhesiveness when applied to the skin, and therefore, it is possible to improve makeup sustainability.

The content of the above-described coated powder in the oily cosmetics can be set to be 0.1 to 65 mass %, 1 to 55 mass %, and 5 to 55 mass % based on the total amount of the oily cosmetics.

The oily cosmetics of the present embodiment can comprise powder other than the above-described coated powder. Any powder exemplified in the above-described base material powder can be used. The total content of the powder in the oily cosmetics of the present embodiment can be set to be 5 to 65 mass %, 10 to 55 mass %, and 20 to 55 mass % based on the total amount of the oily cosmetics.

(Oily Components)

It is possible to use, for example, solid oil or liquid oil used in usual cosmetic products, as oily components, and two or more kinds of oily cosmetics can be blended in combination. The solid oil refers to oil which does not flow when inclined at 40° C. It is possible to use high viscosity liquid oil having a viscosity at 25° C. of greater than or equal to 200 mPa·s and low viscosity liquid oil having a viscosity at 25° C. of less than 200 mPa·s, as the liquid oil.

Examples of the solid oil include paraffin waxes such as petrolatum and polyethylene wax, hydrocarbons such as microcrystalline wax, and polyethylene, vegetable-derived oils and fats such as hydrogenated castor oil, hydrogenated jojoba oil, carnauba wax, and rice wax, esters such as glyceryl tribehenate and cholesterol fatty acid ester, higher fatty acids such as stearic acid and behenic acid, higher alcohols such as stearyl alcohol and behenyl alcohol, silicones such as alkyl-modified silicone and acrylic-modified silicone, and sugar fatty acid esters such as dextrin palmitate and inulin stearate. The solid oils can be used singly or in combination of two or more thereof.

Examples of the liquid oil include hydrocarbon oils such as liquid paraffin and squalane, ester oils such as diisostearyl malate, isopropyl myristate, cetyl 2-ethylhexanoate, isopropyl palmitate, ethylhexyl palmitate, glyceryl tricaprylate/caprate, glyceryl tri-2-ethylhexanoate, and polyglyceryl triisostearate, vegetable oils such as olive oil, castor oil, macadamia nut oil, and jojoba oil, higher alcohols such as oleyl alcohol, octyl dodecanol, and isostearyl alcohol, higher fatty acids such as isostearic acid and oleic acid, and silicone oils such as dimethyl polysiloxane, methylphenyl polysiloxane, and decamethylcyclopentasiloxane. The liquid oils can be used singly or in combination of two or more thereof.

Of the above, examples of the high viscosity liquid oil include diisostearyl malate, castor oil, and polyglyceryl triisostearate.

Of the above, examples of the low viscosity liquid oil include liquid paraffin, squalane, isopropyl myristate, cetyl 2-ethylhexanoate, olive oil, jojoba oil, octyl dodecanol, dimethyl polysiloxane, and decamethylcyclopentasiloxane.

The content of the solid oil in the oily cosmetics of the present embodiment can be set to be 0 to 40 mass %, 0 to 35 mass %, 1 to 30 mass %, and 3 to 30 mass % based on the total amount of the oily cosmetics.

The content of the liquid oil in the oily cosmetics of the present embodiment can be set to be 25 to 95 mass %, 25 to 87 mass %, 25 to 85 mass %, 25 to 75 mass %, and 25 to 65 mass % based on the total amount of the oily cosmetics.

In the oily cosmetics of the present embodiment, the content of the low viscosity liquid oil is preferably 25 to 95 mass % and more preferably 25 to 85 mass % based on the total amount of the oily cosmetics from the viewpoint of usability.

(Other Components)

Other components, for example, a moisturizing agent, a surfactant, an ultraviolet absorber, a film forming agent, a preservative, vitamins, cosmetic ingredients, antioxidants, and perfumes, which are used in usual cosmetic products other than the oily components and the powder components described above, can be appropriately blended with the oily cosmetics of the present embodiment as necessary within the scope not impairing the effect of the present invention.

The application of the oily cosmetics according to the present embodiment is not particularly limited, but examples thereof include makeup cosmetics such as lipstick, foundation, and blush, skin care cosmetics such as eye cream, antiperspirant, and solid perfume, and hair cosmetics such as hair dressing agents.

In addition, the oily cosmetics according to the present embodiment may be solid, that is, oily solid cosmetics. The application in this case is not particularly limited, but preferred examples thereof include makeup cosmetics such as an eyebrow pencil, eyeliner, eye shadow, and foundation.

The oily cosmetics according to the present embodiment may be formed in a stick shape or a pencil shape, and may directly fill a container such as an inner tray.

Examples of the method for producing oily solid cosmetics according to the present embodiment include a method for filling a predetermined container or mold with a bulk amount of cosmetics obtained by mixing the oily components and the powder components described above, and other components as necessary, and solidifying the cosmetic substance. An example of a method of manufacturing oily cosmetics may comprise obtaining coated powder by subjecting a base material powder to a composite treatment using at least alkylsilane and phospholipid through a wet method that continuously presents a liquid solvent while incorporating the alkylsilane and the phospholipid into the base material powder.

It is possible to make the bulk amount of cosmetics comprise a volatile solvent. Examples of the volatile solvent include alcohols such as ethanol, propyl alcohol, and isopropyl alcohol; hydrocarbon solvents such as isododecane and isoparaffin; silicones such as octamethylcyclopentasiloxane, decamethylcyclopentasiloxane, octamethyltrisiloxane, and decamethyltetrasiloxane.

Examples of the predetermined container filled with a cosmetic composition include inner trays such as a metal tray and a resin tray. These inner trays can be mounted in a compact container after the oily solid cosmetics are formed. In addition, it is also possible to directly fill the compact container or a jar container with oily solid cosmetics. Examples of the method for molding cosmetics into a stick shape include a well-known filling molding method or an extrusion molding method.

EXAMPLES

Hereinafter, the present invention will be further described in detail using examples. However, the technical scope of the present invention is not limited by these examples.

<Preparation of Coated Powder>

(Coated Powder W-1)

Composite treatment was performed on titanium oxide which is a base material powder through the following wet method using triethoxycaprylylsilane and lecithin, to obtain coated titanium oxide (coated powder W-1).

First, 1,000 g of titanium oxide (manufactured by ISHIHARA SANGYO KAISHA, LTD., titanium oxide CR-50) was placed in a Henschel mixer. On the other hand, 1.0 g of aluminum chloride was dissolved in a small amount of water, and a triethoxycaprylylsilane solution was prepared which was obtained by adding 20.0 g of triethoxycaprylylsilane (manufactured by Shin-Etsu Chemical Co., Ltd., KBE-3083) and an appropriate amount of isopropyl alcohol thereto and dissolving them therein.

The above-described solution was added dropwise into the Henschel mixer and mixed together while stirring. After checking that the base material powder and the solution were mixed with each other, 70.0 g of 8% ammonia water was added dropwise thereto. After the dropwise addition of the ammonia water, the mixture was further stirred.

Next, 20.0 g of hydrogenated lecithin (manufactured by Nikko Chemicals Co., Ltd., NIKKOL RESINOL S-10) was added to the Henschel mixer, and the stirring was continued. After the addition of lecithin, it was confirmed that the mixture was sufficiently mixed. The interior of the Henschel mixer was heated and depressurized, and isopropyl alcohol, water, and ammonia were removed. After removing the solvent or the like, powder subjected to surface treatment was taken out of the mixer, pulverized, and subjected to heat treatment. In this manner, coated titanium oxide subjected to composite treatment using 2 mass % of triethoxycaprylylsilane and 2 mass % of lecithin was obtained.

(Coated Powder W-2 to W-4)

Coated powders were obtained in the same manner as the coated powder W-1 except that titanium oxide as the base material powder was changed to each of the following coloring pigments.

Coated powder W-2: black iron oxide
Coated Powder W-3: red iron oxide
Coated powder W-4: yellow iron oxide (Coated Powder W-5)

Coated powder W-5 was obtained in the same manner as the coated powder W-1 except that disodium N-stearoyl-L-glutamate (manufactured by AJINOMOTO CO., INC., AMISOFT HS-21) was used instead of lecithin.

(Coated Powder W-6 to W-8)

Coated powders were obtained in the same manner as the coated powder W-5 except that titanium oxide as the base material powder was changed to each of the following coloring pigments.

Coated powder W-6: black iron oxide
Coated Powder W-7: red iron oxide
Coated powder W-8: yellow iron oxide (Coated Powder W-9)

Coated powder W-9 was obtained in the same manner as the coated powder W-1 except that tridecafluorooctyltriethoxysilane (manufactured by Degussa, DYNASYLAN F8261) was used instead of lecithin.

(Coated Powder W-10 to W-12)

Coated powders were obtained in the same manner as the coated powder W-9 except that titanium oxide as the base material powder was changed to each of the following coloring pigments.

Coated powder W-10: black iron oxide
Coated Powder W-11: red iron oxide
Coated powder W-12: yellow iron oxide (Coated Powder W-13)

Coated powder W-13 was obtained in the same manner as the coated powder W-1 except that lecithin was not added thereto.

(Coated Powder W-14 to W-16)

Coated powders were obtained in the same manner as the coated powder W-13 except that titanium oxide as the base material powder was changed to each of the following coloring pigments.

Coated powder W-14: black iron oxide
Coated Powder W-15: red iron oxide
Coated powder W-16: yellow iron oxide (Coated Powder W-17)

1,000 g of titanium oxide was placed in a Henschel mixer. 20.0 g of lecithin and isopropyl alcohol were added thereto and mixed with each other. It was confirmed that the mixture was sufficiently mixed, the interior of the Henschel mixer was heated and depressurized, and isopropyl alcohol was removed. After removing the solvent, powder subjected to surface treatment was taken out of the mixer, pulverized through heat treatment, and subjected to heat treatment to obtain coated powder W-17.

(Coated Powder W-18 to W-20)

Coated powders were obtained in the same manner as the coated powder W-17 except that titanium oxide as the base material powder was changed to each of the following coloring pigments.

Coated powder W-18: black iron oxide
Coated Powder W-19: red iron oxide
Coated powder W-20: yellow iron oxide (Coated Powder D-1)

1,000 g of titanium oxide (manufactured by ISHIHARA SANGYO KAISHA, LTD., titanium oxide CR-50) was placed in a Henschel mixer, 20.0 g of triethoxycaprylylsilane and 20.0 g of lecithin were added thereto, the mixture was dispersed uniformly, and mixing was performed for 30 minutes at 80° C. under reduced pressure. Thereafter, pulverization was performed and coated powder D-1 was obtained.

(Coated Powder D-2 to D-4)

Coated powders were obtained in the same manner as the coated powder D-1 except that titanium oxide as the base material powder was changed to each of the following coloring pigments.

Coated powder D-2: black iron oxide
Coated Powder D-3: red iron oxide
Coated powder D-4: yellow iron oxide Examples 1 to 3 and Comparative Examples 1 to 6

Oily solid cosmetics (eyebrow pencils) were prepared by the formulation (blending amount is on parts by mass basis) shown in Tables 1 to 3 through the following production method.

<Production Method>

Oily components were heated at 95° C., dissolved, and mixed with each other. Powder components were added to the mixture and uniformly dispersed with a stirrer in order to obtain the bulk amount of cosmetics. Thereafter, a mold was filled with a dissolved substance as the bulk amount of cosmetics in a state where the dissolved substance was melted at 95° C. which was then cooled to 25° C. Then, the dissolved substance was taken out and a rod-like eyebrow pencil sample (evaluation sample) was obtained.

Each category of the obtained bulk amount of cosmetics and sample (evaluation sample) was evaluated based on the following evaluation method. The results are shown in Tables 1 to 3.

[Color Floating Due to the Aggregation of Powder During Heating and Melting]

Regarding the melted surface of the bulk amount of cosmetics, a color floating state due to the aggregation of powder was observed and evaluated in four stages.

<Evaluation Criteria>

A: There is no color floating due to the aggregation of powder.

B: There is almost no color floating due to the aggregation of powder.

C: There is color floating due to the aggregation of powder.

D: There are many color floating portions due to the aggregation of powder.

[Viscosity (Filling Property) During Heating and Melting]

The ease of filling a mold with a melted bulk amount of cosmetics was evaluated in four levels.

<Evaluation Criteria>

A: Significantly favorable
B: Favorable
C: The filling is difficult.
D: The filling is significantly difficult.

[Usability]

The usability of the oily cosmetics, such as sufficient coverage and less greasy feeling was evaluated by 10 exclusive panels. The evaluation was performed using five values of 1 point (poor) to 5 points (significantly favorable). An average point value was obtained, and a determination was performed based on the following evaluation criteria.

<Evaluation Criteria>

A: Greater than or equal to 4.0 points
B: Greater than or equal to 3.0 points and less than 4.0 points
C: Greater than or equal to 2.0 points and less than 3.0 points
D: Less than 2.0 points

[Makeup Durability]

The makeup durability (e.g., long-wearing, sufficient adhesive) was evaluated by 10 exclusive panels. The evaluation was performed using five values of 1 point (poor) to 5 points (significantly favorable). An average point value was obtained, and a determination was performed based on the following evaluation criteria.

<Evaluation Criteria>

A: Greater than or equal to 4.0 points
B: Greater than or equal to 3.0 points and less than 4.0 points
C: Greater than or equal to 2.0 points and less than 3.0 points
D: Less than 2.0 points

[Stability]

A sealed glass container was filled with cosmetics and allowed to stand for 24 hours at room temperature. Then, it was allowed to stand for 1 week at 50° C. The appearance was observed and evaluated using four levels.

<Evaluation Criteria>

A: There is no change.
B: There is a slight change.
C: There is a change within an allowable range.
D: There is significant change.

TABLE 1

| | | | Example 1 | Example 2 | Example 3 | Comparative Example 1 |
|---|---|---|---|---|---|---|
| Oily component | Solid oil | Polyethylene wax | 18 | 25 | 14 | 18 |
| | | Candelilla wax | 2 | 3 | 1.5 | 2 |
| | Low viscosity liquid oil | Ethylhexyl palmitate | 5 | 7.5 | 4 | 5 |
| | | Triethylhexanoin | 5 | 7.5 | 4 | 5 |
| | | Dimethicone | 5 | 7.5 | 4 | 5 |
| | | Diethylhexanoic acid Neopentyl glycol | 17.5 | 26 | 14 | 17.5 |
| | High viscosity liquid oil | Sorbitan sesquiisostearate | 5 | 5 | 5 | 5 |
| Powder component | Coated powder | Coated powder W-1 | 5.5 | 2.5 | 8 | — |
| | | Coated powder W-2 | 7 | 3.5 | 11 | — |
| | | Coated powder W-3 | 3 | 1.5 | 4.5 | — |
| | | Coated powder W-4 | 6 | 3 | 9 | — |
| | Other powder | Untreated titanium oxide | — | — | — | 5.5 |
| | | Untreated black iron oxide | — | — | — | 7 |
| | | Untreated red iron | — | — | — | 3 |
| | | Untreated yellow iron oxide | — | — | — | 6 |
| | | Poly(methyl methacrylate) crosspolymer | 15 | 5 | 15 | 15 |
| | | Talc | 3 | 1.5 | 3 | 3 |
| | | Mica | 3 | 1.5 | 3 | 3 |
| | | Total | 100 | 100 | 100 | 100 |
| | | Total amount of powder (mass %) | 42.5 | 18.5 | 53.5 | 42.5 |
| | | Amount of coated powder (mass %) | 21.5 | 10.5 | 32.5 | — |
| | | Amount of untreated powder (mass %) | — | — | — | 21.5 |
| | | Amount of solid oil (mass %) | 20 | 28 | 15.5 | 20 |
| | | Amount of liquid oil (mass %) | 37.5 | 53.5 | 31 | 37.5 |
| | | Amount of low viscosity liquid oil (mass %) | 32.5 | 48.5 | 26 | 32.5 |
| Evaluation | | Color floating due to aggregation of powder during heating and melting | A | A | A | D |
| | | Viscosity (filling property) during heating and melting | A | A | B | D |
| | | Usability | A | A | B | C |
| | | Makeup durability | A | A | A | C |
| | | Stability | A | A | A | C |

TABLE 2

| | | | Comparative Example 2 | Comparative Example 3 |
|---|---|---|---|---|
| Oily component | Solid oil | Polyethylene wax | 18 | 18 |
| | | Candelilla wax | 2 | 2 |

TABLE 2-continued

|  |  |  | Comparative Example 2 | Comparative Example 3 |
|---|---|---|---|---|
|  | Low viscosity liquid oil | Ethylhexyl palmitate | 5 | 5 |
|  |  | Triethylhexanoin | 5 | 5 |
|  |  | Dimethicone | 5 | 5 |
|  |  | Diethylhexanoic acid Neopentyl glycol | 17.5 | 17.5 |
|  | High viscosity liquid oil | Sorbitan sesquiisostearate | 5 | 5 |
| Powder component | Coated powder | Coated powder W-5 | 5.5 | — |
|  |  | Coated powder W-6 | 7 | — |
|  |  | Coated powder W-7 | 3 | — |
|  |  | Coated powder W-8 | 6 | — |
|  |  | Coated powder W-9 | — | 5.5 |
|  |  | Coated powder W-10 | — | 7 |
|  |  | Coated powder W-11 | — | 3 |
|  |  | Coated powder W-12 | — | 6 |
|  | Other powder | Poly(methyl methacrylate) crosspolymer | 15 | 15 |
|  |  | Talc | 3 | 3 |
|  |  | Mica | 3 | 3 |
|  | Total |  | 100 | 100 |
|  | Total amount of powder (mass %) |  | 42.5 | 42.5 |
|  | Amount of coated powder (mass %) |  | 21.5 | 21.5 |
|  | Amount of solid oil (mass %) |  | 20 | 20 |
|  | Amount of liquid oil (mass %) |  | 37.5 | 37.5 |
|  | Amount of low viscosity liquid oil (mass %) |  | 32.5 | 32.5 |
| Evaluation | Color floating due to aggregation of powder during heating and melting |  | C | C |
|  | Viscosity (filling property) during heating and melting |  | C | C |
|  | Usability |  | C | C |
|  | Makeup durability |  | C | B |
|  | Stability |  | A | A |

TABLE 3

|  |  |  | Comparative Example 4 | Comparative Example 5 | Comparative Example 6 |
|---|---|---|---|---|---|
| Oily component | Solid oil | Polyethylene wax | 18 | 18 | 18 |
|  |  | Candelilla wax | 2 | 2 | 2 |
|  | Low viscosity liquid oil | Ethylhexyl palmitate | 5 | 5 | 5 |
|  |  | Triethylhexanoin | 5 | 5 | 5 |
|  |  | Dimethicone | 5 | 5 | 5 |
|  |  | Diethylhexanoic acid Neopentyl glycol | 17.5 | 17.5 | 17.5 |
|  | High viscosity liquid oil | Sorbitan sesquiisostearate | 5 | 5 | 5 |
| Powder component | Coated powder | Coated powder W-13 | 5.5 | — | — |
|  |  | Coated powder W-14 | 7 | — | — |
|  |  | Coated powder W-15 | 3 | — | — |
|  |  | Coated powder W-16 | 6 | — | — |
|  |  | Coated powder W-17 | — | 5.5 | — |
|  |  | Coated powder W-18 | — | 7 | — |
|  |  | Coated powder W-19 | — | 3 | — |
|  |  | Coated powder W-20 | — | 6 | — |
|  |  | Coated powder D-1 | — | — | 5.5 |
|  |  | Coated powder D-2 | — | — | 7 |
|  |  | Coated powder D-3 | — | — | 3 |
|  |  | Coated powder D-4 | — | — | 6 |
|  | Other powder | Poly(methyl methacrylate) crosspolymer | 15 | 15 | 15 |
|  |  | Talc | 3 | 3 | 3 |
|  |  | Mica | 3 | 3 | 3 |
|  | Total |  | 100 | 100 | 100 |
|  | Total amount of powder (mass %) |  | 42.5 | 42.5 | 42.5 |
|  | Amount of coated powder (mass %) |  | 21.5 | 21.5 | 21.5 |
|  | Amount of solid oil (mass %) |  | 20 | 20 | 20 |
|  | Amount of liquid oil (mass %) |  | 37.5 | 37.5 | 37.5 |
|  | Amount of low viscosity liquid oil (mass %) |  | 32.5 | 32.5 | 32.5 |

TABLE 3-continued

|  |  | Comparative Example 4 | Comparative Example 5 | Comparative Example 6 |
|---|---|---|---|---|
| Evaluation | Color floating due to aggregation of powder during heating and melting | C | C | C |
|  | Viscosity (filling property) during heating and melting | C | C | C |
|  | Usability | B | C | C |
|  | Makeup durability | A | D | B |
|  | Stability | A | A | D |

As shown in Tables 1 to 3, favorable results were obtained from the oily solid cosmetics (eyebrow pencils) of Examples 1 to 3 which comprise the coated powder according to the present invention in all evaluation categories of the color floating due to the aggregation of powder during heating and melting, the viscosity (filling property) during heating and melting, the usability, the makeup durability, and the stability. On the other hand, oily solid cosmetics (eyebrow pencils) in Comparative Examples 1 to 6 which do not comprise the coated powder according to the present invention could not satisfy all the evaluation categories.

Specifically, in the oily solid cosmetics of Comparative Example 1 in which untreated powder was used instead of coated powder, there were problems in the color floating due to the aggregation of powder during heating and melting, the viscosity (filling property) during heating and melting, the usability, and the makeup durability. In the oily solid cosmetics of Comparative Examples 2 and 3 in which powder, of which hydrogenated lecithin for composite treatment was changed to other treatment agents, was used, there were problems in the color floating due to the aggregation of powder during heating and melting, the viscosity (filling property) during heating and melting, and the usability. The oily solid cosmetics of Comparative Example 4 in which powder treated with alkylsilane alone instead of the composite treatment were satisfactory in the makeup durability, but there were problems in the color floating due to the aggregation of powder during heating and melting and the viscosity (filling property) during heating and melting. The oily solid cosmetics of Comparative Example 5 in which powder treated with hydrogenated lecithin alone was used had a particularly unfavorable result in the makeup durability. In the oily solid cosmetics of Comparative Example 6 in which coated powder produced through a dry method was used, there was a problem in the stability.

Example 4: Eyeliner Pencil

| (Component) | (blending ratio (mass %)) |
|---|---|
| 1. Polyethylene wax | 4.00 |
| 2. Candelilla row | 9.00 |
| 3. Diglyceryl triisostearate | 2.16 |
| 4. Tocopherol | 0.04 |
| 5. Dimethicone | 21.00 |
| 6. Diisostearyl malate | 8.00 |
| 7. Trimethylsiloxysilicate | 25.00 |
| 8. Synthetic phlogopite | 2.50 |
| 9. Coated powder W-1 | 0.10 |
| 10. Coated powder W-2 | 25.00 |
| 11. Coated powder W-3 | 0.10 |
| 12. Coated powder W-4 | 0.10 |
| 13. Silica | 3.00 |

<Production Method>

Oily components 1 to 7 were heated at 95° C., dissolved, and mixed with each other. Powder components 8 to 13 were added to the mixture and uniformly dispersed with a stirrer. Thereafter, a mold was filled with the dissolved substance as the bulk amount of cosmetics in a state where the dissolved substance was melted at 95° C. which was then cooled to 25° C. Then, the dissolved substance was taken out and a rod-like eyeliner pencil sample was obtained.

<Evaluation>

The obtained eyeliner pencil sample was evaluated in the same manner as described above, and it was confirmed that the sample was evaluated as "A" in all categories of "Color floating due to aggregation of powder during heating and melting", "Viscosity (filling property) during heating and melting", "Usability", "Makeup durability", and "Stability".

Example 5: Eyeliner Pencil

| (Component) | (blending ratio (mass %)) |
|---|---|
| 1. Polyethylene wax | 2.00 |
| 2. Candelilla row | 9.00 |
| 3. Triethylhexanoin | 4.86 |
| 4. Tocopherol | 0.04 |
| 5. Microcrystalline wax | 0.04 |
| 6. Methyl trimethicone | 25.00 |
| 7. Sorbitan sesquiisostearate | 1.00 |
| 8. Trimethylsiloxysilicate | 18.00 |
| 9. Mica | 9.50 |
| 10. Coated powder W-1 | 0.10 |
| 11. Coated powder W-2 | 10.00 |
| 12. Coated powder W-3 | 7.50 |
| 13. Coated powder W-4 | 6.00 |
| 14. Polymethyl methacrylate crosspolymer | 3.00 |

<Production Method>

Oily components 1 to 8 were heated at 95° C., dissolved, and mixed with each other. Powder components 10 to 14 were added to the mixture and uniformly dispersed with a stirrer. Thereafter, a mold was filled with the dissolved substance as the bulk amount of cosmetics, in a state where the dissolved substance was melted at 95° C. which was then cooled to 25° C. Then, the dissolved substance was taken out and a rod-like eyeliner pencil sample was obtained.

<Evaluation>

The obtained eyeliner pencil sample was evaluated in the same manner as described above, and it was confirmed that the sample was evaluated as "A" in all categories of "Color floating due to aggregation of powder during heating and melting", "Viscosity (filling property) during heating and melting", "Usability", "Makeup durability", and "Stability".

Example 6: Gel Eyeliner

| (Component) | (blending ratio (mass %)) |
|---|---|
| 1. Inulin stearate | 6.00 |
| 2. Sunflower seed raw | 2.00 |
| 3. Paraffin wax | 8.00 |
| 4. Diglyceryl triisostearate | 1.50 |
| 5. Neopentyl glycol diethylhexanoate | 3.36 |
| 6. Tocopherol | 0.04 |
| 7. Microcrystalline wax | 4.00 |
| 8. Methyl trimethicone | 25.00 |
| 9. Sorbitan sesquiisostearate | 1.00 |
| 10. Trimethylsiloxysilicate | 9.00 |
| 11. Mica | 20.00 |
| 12. Coated powder W-1 | 0.50 |
| 13. Coated powder W-2 | 5.30 |
| 14. Coated powder W-3 | 6.30 |
| 15. Coated powder W-4 | 7.00 |
| 16. Silica | 1.00 |

<Production Method>

Oily components 1 to 10 were heated at 95° C., dissolved, and mixed with each other. Powder components 11 to 16 were added to the mixture and uniformly dispersed with a stirrer. Thereafter, a jar container was filled with the dissolved substance as the bulk amount of cosmetics in a state where the dissolved substance was melted at 95° C. which was then cooled. Then, a gel-like eyeliner sample was obtained.

<Evaluation>

The obtained gel eyeliner sample was evaluated in the same manner as described above, and it was confirmed that the sample was evaluated as "A" in all categories of "Color floating due to aggregation of powder during heating and melting", "Viscosity (filling property) during heating and melting", "Usability", "Makeup durability", and "Stability".

Example 7: Lipstick

| (Component) | (blending ratio (mass %)) |
|---|---|
| 1. Polyethylene wax | 5.50 |
| 2. Diisostearyl malate | 23.19 |
| 3. Diphenylsiloxy phenyl trimethicone | 4.50 |
| 4. Isotridecyl isononanoate | 4.50 |
| 5. Olefin oligomer | 9.00 |
| 6. Hydrogenated polyisobutene | 35.00 |
| 7. Dimethylsilylated silica | 1.00 |
| 8. Simethicone | 0.02 |
| 9. Tocopherol | 0.04 |
| 10. Dimerdilinoleic acid (Phytosteryl/isostearyl/cetyl/stearyl/behenyl) (solid oil having melting point around 40° C.) | 13.00 |
| 11. Coated powder W-21 | 0.20 |
| 12. Coated powder W-22 | 0.50 |
| 13. Coated powder W-1 | 0.70 |
| 14. Coated powder W-4 | 0.10 |
| 15. Coated powder W-3 | 0.20 |
| 16. Red No. 218 | 0.05 |
| 17. Titanium mica | 0.50 |
| 18. Borosilicate (Ca/Al) | 0.20 |

The coated powder W-21 is coated powder produced similarly to the coated powder W-1 except that titanium oxide as the base material powder was changed to Red No. 202. In addition, the coated powder W-22 is coated powder produced similarly to the coated powder W-1 except that titanium oxide as the base material powder was changed to Yellow No. 4 Aluminum Lake.

<Production Method>

Oily components 1 to 6 and 8 to 10 were heated at 95° C., dissolved, and mixed with each other. Powder components 7 and 11 to 18 were added to the mixture and uniformly dispersed with a stirrer. Thereafter, a mold was filled with the dissolved substance as the bulk amount of cosmetics in a state where the dissolved substance was melted at 95° C. which was then cooled to 25° C. Then, a rod-like lipstick sample was obtained.

<Evaluation>

The obtained lipstick sample was evaluated in the same manner as described above, and it was confirmed that the sample was evaluated as "A" in all categories of "Color floating due to aggregation of powder during heating and melting", "Viscosity (filling property) during heating and melting", "Usability", "Makeup durability", and "Stability".

Example 8: Eyebrow Pencil

| (Component) | (blending ratio (mass %)) |
|---|---|
| 1. Hydrogenated castor oil | 8.00 |
| 2. Japan wax | 9.00 |
| 3. Stearic acid | 15.00 |
| 4. Bees wax | 3.00 |
| 5. Hydrogenated oil | 2.00 |
| 6. Mineral oil | 1.68 |
| 7. Sorbitan isostearate | 1.00 |
| 8. Tocopherol | 0.02 |
| 9. Talc | 5.00 |
| 10. Mica | 4.80 |
| 11. Coated powder W-23 | 0.20 |
| 12. Coated powder W-1 | 22.00 |
| 13. Coated powder W-4 | 13.50 |
| 14. Coated powder W-3 | 8.50 |
| 15. Coated powder W-2 | 6.30 |

The coated powder W-23 is coated powder produced similarly to the coated powder W-1 except that titanium oxide as the base material powder was changed to ultramarine blue.

<Production Method>

Oily components 1 to 8 were heated at 95° C., dissolved, and mixed with each other. Powder components 9 to 15 were added to the mixture and uniformly dispersed with a stirrer. Thereafter, extrusion molding was performed to obtain a rod-like eyebrow pencil.

<Evaluation>

The obtained eyebrow pencil sample was evaluated in the same manner as described above, and it was confirmed that the sample was evaluated as "A" in all categories of "Color floating due to the aggregation of powder during heating and melting", "Viscosity (filling property) during heating and melting", "Usability", "Makeup durability", and "Stability".

Example 9: Blush

| (Component) | (blending ratio (mass %)) |
|---|---|
| 1. Polyethylene wax | 5.00 |
| 2. Glyceryl tricaprylate/tricaprate | 18.00 |
| 3. Diphenylsiloxy phenyl trimethicone | 15.00 |

-continued

| (Component) | (blending ratio (mass %)) |
|---|---|
| 4. Hydrogenated polyisobutene | 15.00 |
| 5. Dimerdilinoleic acid Dimerdilinoleic acid bis(behenyl/isostearyl/phytosteryl) (solid oil having melting point around 40° C.) | 13.00 |
| 6. Diisostearyl malate | 26.349 |
| 7. Tocopherol | 0.02 |
| 8. Simethicone | 0.001 |
| 9. Dimethylsilylated silica | 0.10 |
| 10. Coated powder W-21 | 0.50 |
| 11. Coated powder W-22 | 3.00 |
| 12. Coated powder W-1 | 4.00 |
| 13. Coated powder W-4 | 0.01 |
| 14. Coated powder W-3 | 0.01 |
| 15. Coated powder W-2 | 0.01 |

<Production Method>

Oily components 1 to 8 were heated at 95° C., dissolved, and mixed with each other. Powder components 9 to 15 were added to the mixture and uniformly dispersed with a stirrer. Thereafter, an inner tray was filled with the dissolved substance as the bulk amount of cosmetics in a state where the dissolved substance was melted at 95° C. which was then cooled to 25° C. Then, an oily solid-like blush sample was obtained.

<Evaluation>

The obtained blush sample was evaluated in the same manner as described above, and it was confirmed that the sample was evaluated as "A" in all categories of "Color floating due to the aggregation of powder during heating and melting", "Viscosity (filling property) during heating and melting", "Usability", "Makeup durability", and "Stability".

Example 10: Foundation (Oily Liquid Type)

| (Component) | (blending ratio (mass %)) |
|---|---|
| 1. Dimethicone | 16.00 |
| 2. Polymethylsilsesquioxane | 3.00 |
| 3. Dimethicone/vinyl dimethicone) crosspolymer | 1.50 |
| 4. Cetyl ethylhexanoate | 18.00 |
| 5. Triisostearin | 22.00 |
| 6. Diisostearyl malate | 13.64 |
| 7. PEG-9 polydimethylsiloxyethyl dimethicone | 3.00 |
| 8. Sorbitan sesquioleate | 0.50 |
| 9. Tocopherol | 0.04 |
| 10. Synthetic phlogopite | 7.00 |
| 11. Nylon | 4.00 |
| 12. Coated powder W-24 | 5.00 |
| 13. Coated powder W-1 | 5.60 |
| 14. Coated powder W-4 | 0.55 |
| 15. Coated powder W-3 | 0.12 |
| 16. Coated powder W-2 | 0.05 |

The coated powder W-24 is coated powder produced similarly to the coated powder W-1 except that titanium oxide as the base material powder was changed to particulate titanium oxide (manufactured by ISHIHARA SANGYO KAISHA, LTD., ultrafine particle titanium oxide TTO-V-4) having an average particle diameter of 0.06 μm on a major axis and 0.01 μm on a minor axis.

<Production Method>

Oily components 1 to 9 were mixed with each other. Powder components 10 to 16 were added to the mixture and uniformly dispersed with a stirrer. Thereafter, a bottle container was filled with the mixture at room temperature to obtain a bottle-like foundation sample.

<Evaluation>

The obtained foundation sample was evaluated in the same manner as described above, and it was confirmed that the sample was evaluated as "A" in all categories of "Color floating due to the aggregation of powder at room temperature", "Viscosity (filling property) at room temperature", "Usability", "Makeup durability", and "Stability".

Example 11: Lip Gloss

| (Component) | (blending ratio (mass %)) |
|---|---|
| 1. Dextrin palmitate | 6.50 |
| 2. Ethylhexyl palmitate | 10.00 |
| 3. Diisostearyl malate | 38.96 |
| 4. Hydrogenated polyisobutene | 40.00 |
| 5. Phenoxyethanol | 0.50 |
| 6. Tocopherol | 0.04 |
| 7. Dimethicone | 0.10 |
| 8. Dimethylsilylated silica | 2.00 |
| 9. Coated powder W-25 | 0.30 |
| 10. Coated powder W-1 | 0.70 |
| 11. Coated powder W-4 | 0.30 |
| 12. Coated powder W-3 | 0.05 |
| 13. Coated powder W-2 | 0.05 |
| 14. Titanium mica | 0.50 |

The coated powder W-25 is coated powder produced similarly to the coated powder W-1 except that titanium oxide as the base material powder was changed to carmine.

<Production Method>

Oily components 1 to 7 were heated at 95° C., dissolved, and mixed with each other. Powder components 8 to 14 were added to the mixture and uniformly dispersed with a stirrer. Thereafter, an inner tray was filled with the dissolved substance as the bulk amount of cosmetics in a state where the dissolved substance was melted at 95° C. which was then cooled to 25° C. Then, an oily solid-like lip gloss sample was obtained.

<Evaluation>

The obtained lip gloss sample was evaluated in the same manner as described above, and it was confirmed that the sample was evaluated as "A" in all categories of "Color floating due to the aggregation of powder during heating and melting", "Viscosity (filling property) during heating and melting", "Usability", "Makeup durability", and "Stability".

Example 12: Concealer

| (Component) | (blending ratio (mass %)) |
|---|---|
| 1. Dextrin palmitate | 4.00 |
| 2. Triethythexanoin | 18.00 |
| 3. Neopentyl glycol diethylhexanoate | 3.00 |
| 4. Hydrogenated polydecene | 6.00 |
| 5. Methyl trimethicone | 26.50 |
| 6. Diisostearyl malate | 5.00 |
| 7. (Vinyl dimethicone/lauryl dimethicone) crosspolymer | 7.50 |
| 8. Synthetic phlogopite | 7.15 |
| 9. (Vinyl dimethicone/methicone silsesquioxane) crosspolymer | 5.00 |
| 10. Coated powder W-1 | 15.00 |
| 11. Coated powder W-4 | 2.40 |

-continued

| (Component) | (blending ratio (mass %)) |
|---|---|
| 12. Coated powder W-3 | 0.30 |
| 13. Coated powder W-2 | 0.15 |

<Production Method>

Oily components 1 to 7 were heated at 95° C., dissolved, and mixed with each other. Powder components 8 to 13 were added to the mixture and uniformly dispersed with a stirrer. Thereafter, a jar container was filled with the dissolved substance as the bulk amount of cosmetics in a state where the dissolved substance was melted at 95° C. to obtain an oily solid-like concealer sample.

<Evaluation>

The obtained concealer sample was evaluated in the same manner as described above, and it was confirmed that the sample was evaluated as "A" in all categories of "Color floating due to the aggregation of powder during heating and melting", "Viscosity (filling property) during heating and melting", "Usability", "Makeup durability", and "Stability".

It is to be understood that not all aspects, advantages and features described herein may necessarily be achieved by, or included in, any one particular example embodiment. Indeed, having described and illustrated various examples herein, it should be apparent that other examples may be modified in arrangement and detail. We claim all modifications and variations coming within the spirit and scope of the subject matter claimed herein.

The invention claimed is:

1. Oily cosmetics comprising:
an oily component; and
a powder component comprising coated powder obtained by subjecting base material powder to a composite treatment using at least alkylsilane and phospholipid through a wet method including a wet solvent that is continuously present while the alkylsilane and the phospholipid are layered onto the base material powder,
wherein a coating layer comprising a mixture of the alkylsilane and the phospholipid covers a surface of the base material powder.

2. The oily cosmetics according to claim 1,
wherein a content of the powder component is 5 to 65 mass % based on a total amount of the oily cosmetics,
wherein the oily component comprises:
solid oil in an amount from 0 to 40 mass %, based on the total amount of the oily cosmetics, and
liquid oil in an amount 25 to 95 mass % based on the total amount of the oily cosmetics, and
wherein a content of the coated powder is 0.1 to 65 mass % based on the total amount of the oily cosmetics.

3. The oily cosmetics according to claim 2, wherein the oily cosmetics are oily solid cosmetics.

4. The oily cosmetics according to claim 1, wherein the oily cosmetics are oily solid cosmetics.

5. The oily cosmetics according to claim 1,
wherein a content of the alkylsilane layered onto the base material powder is 1 to 5 parts by mass with respect to 100 parts by mass of the base material powder, and
wherein a content of the phospholipid layered onto the base material powder is 1 to 5 parts by mass with respect to 100 parts by mass of the base material powder.

6. The oily cosmetics according to claim 1, wherein a mass ratio (A/B) of a content A of the alkylsilane to a content B of the phospholipid is 0.2 to 5.

7. The oily cosmetics according to claim 2, wherein the oily component comprises:
solid oil in an amount from 3 to 30 mass %, based on the total amount of the oily cosmetics, and
liquid oil in an amount from 25 to 65 mass % based on the total amount of the oily cosmetics.

8. The oily cosmetics according to claim 1, wherein the alkylsilane is at least one compound selected from a group consisting of triethoxycaprylylsilane and trimethoxycaprylylsilane.

9. The oily cosmetics according to claim 1, wherein the phospholipid comprises lecithin.

10. The oily cosmetics according to claim 1, wherein the surface of the base material powder is uniformly covered with the coating layer.

11. A method of manufacturing oily cosmetics comprising:
obtaining coated powder by subjecting a base material powder to a composite treatment using at least alkylsilane and phospholipid through a wet method including a wet solvent that is continuously present while layering the alkylsilane and the phospholipid onto the base material powder,
wherein a coating layer comprising a mixture of the alkylsilane and the phospholipid covers a surface of the base material powder; and
mixing at least an oily component and a powder component comprising the coated powder.

12. The method of manufacturing oily cosmetics according to claim 11, wherein an amount of the powder component is 5 to 65 mass % based on a total amount of the oily cosmetics,
wherein the oily component comprises:
solid oil in an amount from 0 to 40 mass %, based on a total amount of the oily cosmetics, and
liquid oil in an amount from 25 to 95 mass % based on the total amount of the oily cosmetics, and
wherein a content of the coated powder is 0.1 to 65 mass % based on the total amount of the oily cosmetics.

13. The method of manufacturing oily cosmetics according to claim 11, wherein an amount of the alkylsilane layered onto the base material powder is 1 to 5 parts by mass with respect to 100 parts by mass of the base material powder, and an amount of the base material is 1 to 5 parts by mass with respect to 100 parts by mass of the base material.

14. The method of manufacturing oily cosmetics according to claim 11, wherein a mass ratio (A/B) of an amount of the alkylsilane to an amount of the phospholipid is 0.2 to 5.

15. The method of manufacturing oily cosmetics according to claim 11, wherein the oily component comprises:
solid oil in an amount from 3 to 30 mass %, based on a total amount of the oily cosmetics, and
liquid oil in an amount from 25 to 65 mass % based on the total amount of the oily cosmetics.

16. The method of manufacturing oily cosmetics according to claim 11, wherein the alkylsilane is at least one compound selected from a group consisting of triethoxycaprylylsilane and trimethoxycaprylylsilane.

17. The method of manufacturing oily cosmetics according to claim 11, wherein the phospholipid comprises lecithin.

18. The method of manufacturing oily cosmetics according to claim 11, wherein the surface of the base material is uniformly covered with the coating layer.

\* \* \* \* \*